United States Patent
Kumar et al.

(10) Patent No.: US 6,610,063 B2
(45) Date of Patent: Aug. 26, 2003

(54) SPINAL FIXATION SYSTEM

(75) Inventors: Kris G. Kumar, Raynham, MA (US); Balaji S. Ramamurti, West Chester, PA (US); Barclay R. Davis, Downingtown, PA (US); Thomas J. Runco, Wayne, PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/915,572

(22) Filed: Jul. 27, 2001

(65) Prior Publication Data

US 2002/0035365 A1 Mar. 21, 2002

Related U.S. Application Data (60) Provisional application No. 60/221,518, filed on Jul. 28, 2000.

(51) Int. Cl.[7] .............................................. A61B 17/70
(52) U.S. Cl. ....................................................... 606/61
(58) Field of Search .............................. 606/60, 61, 69, 606/71, 72

(56) References Cited

U.S. PATENT DOCUMENTS

| | | | |
|---|---|---|---|
| 2,439,995 A | 4/1948 | Thrailkill | |
| 3,997,138 A | * 12/1976 | Crock et al. | |
| 4,382,438 A | 5/1983 | Jacobs | |
| 4,653,481 A | 3/1987 | Howland et al. | |
| 4,978,348 A | 12/1990 | Ilizarov | 606/57 |
| 5,002,542 A | 3/1991 | Frigg | 606/61 |
| 5,005,562 A | 4/1991 | Cotrel | 128/69 |
| 5,030,220 A | * 7/1991 | Howland | 606/61 |
| 5,047,029 A | 9/1991 | Aebi et al. | 606/61 |
| 5,246,442 A | 9/1993 | Ashman et al. | 606/61 |
| 5,257,993 A | 11/1993 | Asher et al. | 606/61 |
| 5,263,954 A | 11/1993 | Schlapfer et al. | 606/61 |
| 5,282,801 A | 2/1994 | Sherman | 606/61 |
| 5,312,402 A | 5/1994 | Schläpfer et al. | 606/53 |
| 5,330,473 A | * 7/1994 | Howland | 606/61 |
| 5,344,422 A | 9/1994 | Frigg | 606/61 |
| 5,346,493 A | 9/1994 | Stahurski et al. | 606/61 |
| 5,403,316 A | 4/1995 | Ashman | 606/61 |
| 5,423,818 A | 6/1995 | Van Hoeck et al. | 606/61 |
| 5,437,670 A | 8/1995 | Sherman et al. | 606/61 |
| 5,451,225 A | 9/1995 | Ross, Jr. et al. | 606/59 |
| 5,487,742 A | 1/1996 | Cotrel | 606/61 |

(List continued on next page.)

FOREIGN PATENT DOCUMENTS

| | | |
|---|---|---|
| DE | G 91 01 321.6 | 6/1991 |
| DE | 298 18 831 U 1 | 12/1998 |
| DE | 197 26 754 A 1 | 2/1999 |
| EP | 0 384 001 B1 | 12/1993 |
| EP | 0 838 196 A2 | 4/1998 |
| FR | 2 704 133 | 10/1994 |
| FR | 2 761 256 | 10/1998 |
| WO | WO 88/01152 | 2/1988 |

(List continued on next page.)

*Primary Examiner*—Ralph A. Lewis
(74) *Attorney, Agent, or Firm*—Pennie & Edmonds LLP (57) ABSTRACT

The present invention relates to a fastener assembly for a spinal fixation system and is particularly useful in treatment of pediatric and small-statured patients. The fastener assembly includes a fastener, an attachment member, and a locking member. The fastener has a lower portion for contacting a bone and a upper portion integral with the lower portion and having two open channels. Each channel is configured and dimensioned for receiving a portion of the longitudinal member along its circumference. The attachment member is positionable on the fastener and at least partially covers the channel that receives the longitudinal member. The attachment member is configured and dimensioned for receiving another portion of the longitudinal member along its circumference. The locking member is operatively associated with the upper portion of the fastener and secures the attachment member and longitudinal member to the fastener.

28 Claims, 7 Drawing Sheets

U.S. PATENT DOCUMENTS

| | | | |
|---|---|---|---|
| 5,498,264 A | 3/1996 | Schlapfer et al. | 606/72 |
| 5,501,684 A | 3/1996 | Schlapfer et al. | 606/73 |
| 5,520,689 A | 5/1996 | Schläpfer et al. | 606/61 |
| 5,534,001 A | 7/1996 | Schlapfer et al. | 606/61 |
| 5,545,167 A | 8/1996 | Lin | 606/61 |
| 5,584,832 A | 12/1996 | Schläpfer | 606/61 |
| 5,593,407 A | 1/1997 | Reis | 606/61 |
| 5,601,552 A | 2/1997 | Cotrel | 606/61 |
| 5,624,441 A | 4/1997 | Sherman et al. | 606/61 |
| 5,624,442 A | 4/1997 | Mellinger et al. | 606/61 |
| 5,630,814 A | 5/1997 | Ross, Jr. et al. | 606/59 |
| 5,630,816 A | 5/1997 | Kambin | 606/61 |
| 5,651,789 A | 7/1997 | Cotrel | 606/61 |
| 5,676,665 A | 10/1997 | Bryan | 606/61 |
| 5,683,393 A | 11/1997 | Ralph | 606/61 |
| 5,688,273 A | 11/1997 | Errico et al. | 606/61 |
| 5,688,274 A | 11/1997 | Errico et al. | 606/61 |
| 5,716,355 A | 2/1998 | Jackson et al. | 606/61 |
| 5,738,685 A | 4/1998 | Halm et al. | 606/61 |
| 5,741,254 A | 4/1998 | Henry et al. | 606/61 |
| 5,743,911 A | 4/1998 | Cotrel | 606/61 |
| 5,810,817 A | 9/1998 | Roussouly et al. | 606/61 |
| 5,860,893 A | 1/1999 | watterson et al. | 482/54 |
| 5,863,293 A | 1/1999 | Richelsoph | 606/61 |
| 5,899,903 A | 5/1999 | Cotrel | 606/61 |
| 5,947,966 A | 9/1999 | Drewry et al. | 606/61 |
| 5,964,760 A | 10/1999 | Richelsoph | 606/61 |
| 5,980,523 A | 11/1999 | Jackson | 606/61 |
| 6,206,879 B1 * | 3/2001 | Marnay et al. | 606/53 |
| 6,248,104 B1 | 6/2001 | Chopin et al. | 606/61 |
| WO | WO 98/49960 | 11/1998 | |
| WO | WO 99/04717 | 2/1999 | |
| WO | WO 99/15094 | 4/1999 | |

* cited by examiner

SPINAL FIXATION SYSTEM

RELATED APPLICATION

This application claims the benefit of U.S. Provisional Application No. 60/221,518, filed Jul. 28, 2000.

FIELD OF THE INVENTION

The present invention relates to a spinal fixation system, and in particular to a fastener assembly for securing a longitudinal support along a spinal column.

1. Background of Invention

Stabilization of the spine is often required following trauma, tumor, or degenerative pathologies. Each region of the spine presents unique clinical challenges as several vital neural and vascular structures including the vertebral arteries, nerve roots, and spinal cord must be avoided during surgery. The anatomy of pediatric and small-statured patients presents additional challenges that makes assisting such patients even more difficult. For example, because these patients are small in stature, lower profile systems are required. Also, it may be required to add fastener assemblies to an already assembled system, especially in pediatric patients. At the same time, it is desirous to keep inventory at a minimum and have an assembly that requires as few components as possible.

Current methods of spinal fixation are not particularly well-suited for smaller statured patients. U.S. Pat. No. 5,737,685 to Hahn et al. discloses a bone screw that has a threaded shaft and a fork head. The fork head has two legs which define a single groove that opens in the vertical direction for receiving a corrective pin. The upper end of the fork head has an outside thread and a head nut is screwed onto the outer thread. The head nut has inner threads which a fastening screw is screwed to press onto the corrective pin. Because the groove opens in a vertical direction it is difficult to add additional screws to an already installed fixation system.

U.S. Pat. No. 5,530,441 to Sherman et al. discloses an attachment plate configured for use with a spinal fixation element that has a posteriorly projecting central post. The attachment plate is generally L-shaped with an eyebolt engaging portion and a fixation element clamping portion. The fixation element has grooves in the lateral surfaces of the central post and one lateral surface of the post contacts the spinal rod when the rod extends through an aperture of an eyebolt assembly. A flange extends from the attachment plate and is configured to engage the opposite lateral surface of the post and the attachment plate includes a camming segment to provide a clamping force component directed toward the flange to clamp the spinal rod to the fixation element post when a nut is threaded onto the eyebolt threaded post. The attachment plate has a slot in the eyebolt engaging portion for receiving the posteriorly projecting threaded post of the eyebolt body. Because the eyebolt must be pre-assembled onto the spinal rod, it is difficult to add additional fixation elements to an already installed system.

U.S. Pat. No. 4,653,481 to Howland et al. discloses a spinal support system that includes a plurality of screw clamp assemblies. Each screw clamp assembly has a threaded end for placement into the vertebra and a saddle assembly removably attached to the screw formed of upper and lower halves. Each of the upper and lower halves of the saddle assembly are provided with at least one pair of mating grooves for accepting a spinal rod. All embodiments shown and described in the Howland '481 patent have a two-part saddle assembly that is removable from the screw clamp shaft member.

As the discussion above illustrates, there is a need for an improved fixation apparatus for stabilizing the spine that can be assembled to an already installed fixation system and has minimal components.

2. Summary of Invention

The present invention relates to a fastener assembly for a spinal fixation system. The fastener assembly includes a fastener, an attachment member, and a locking member. The fastener has a lower portion for contacting a bone and a upper portion integral with the lower portion and having two open channels. Each channel is configured and dimensioned for receiving a portion of the longitudinal member along its circumference. The attachment member is positionable on the fastener and at least partially covers the channel that receives the longitudinal member. The attachment member is configured and dimensioned for receiving another portion of the longitudinal member along its circumference. The locking member is operatively associated with the upper portion of the fastener and secures the attachment member and longitudinal member to the fastener.

The fastener can be a hook or a screw with the lower portion having a threaded end for engaging a vertebra. If the fastener is a hook, the hook can be provided with an arcuate portion and a flat portion for facilitating implantation. The arcuate portion can have a dimple on a posterior surface to further facilitate implantation. In one embodiment, the locking member is a nut and the upper portion of the fastener has a shaft with external threads to accept the locking member.

The two channels of the fastener are preferably disposed on opposite sides of a central plane of the fastener with the two channels extending orthogonally with respect to the fastener longitudinal axis and equidistant from the proximal end of the fastener. A bore can be positioned transversely to the longitudinal axis and between the two channels.

In an exemplary embodiment, the attachment member includes a cylinder having upper, lower, and side surfaces with a bore extending through the upper and lower surfaces and defining a longitudinal axis lying in a central plane; a slot extending through the cylinder offset from the central plane and parallel with the central plane; and a protrusion extending from the bottom surface on an opposite side of the central plane from the slot. The channels can define a seat for accepting the protrusion of the attachment member. The slot can be provided with serrations along the inner surface. The slot can also have an eccentric cross-sectional shape with a geometry substantially conforming to a diameter of the longitudinal member.

The fastener can have a cavity extending longitudinally from the distal end for receiving a manipulation device. This manipulation device includes a ball detent mechanism and a groove extending transversely to the cavity and around its circumference for receiving the ball detent mechanism. Alternatively, the manipulation device has a threaded end and the cavity of the fastener is cylindrical and includes threads along the interior.

DETAILED DESCRIPTION OF THE PREFERRED EMBODIMENTS

Figure 1:
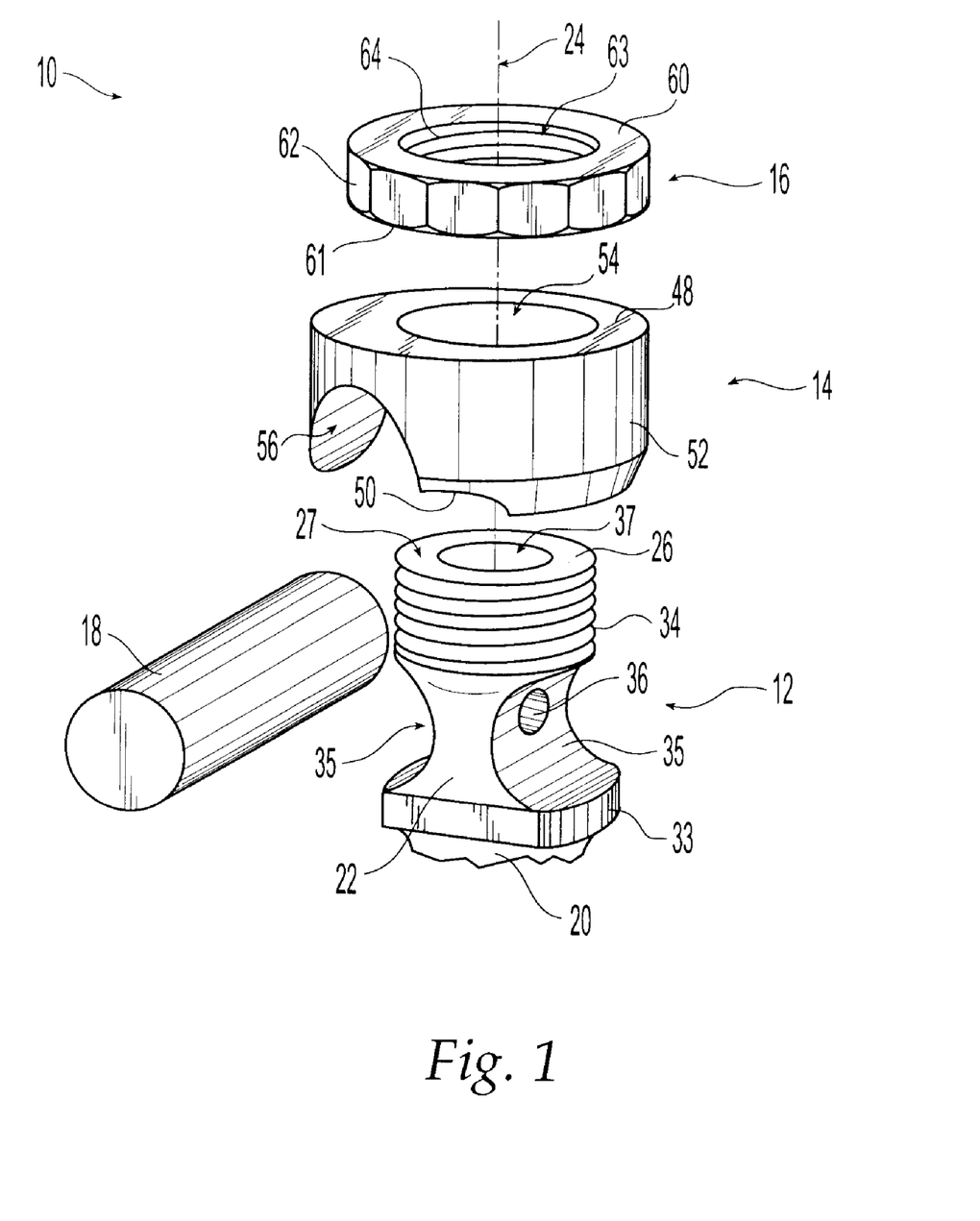
FIG. 1 is an exploded perspective view of a fastener assembly according to the present invention.

Referring to FIG. 1, the fastener assembly 10 according to the invention generally includes a fastener 12, an attachment member 14 positionable on fastener 12 and a locking member 16 securable upon fastener 12. The fastener assembly 10 may be used in a spinal fixation system to secure a longitudinal member 18, such as a rod, along a spinal column. Fastener 12 has a lower portion 20 for engaging a vertebra, and an upper portion 22 integral with lower portion 20 for securing the longitudinal member 18 to fastener 12.

Figure 2:
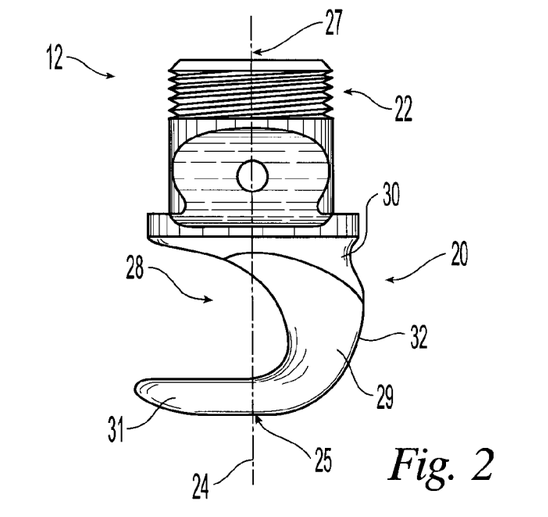
FIG. 2 is a side view of one embodiment of a fastener for the fastener assembly of FIG. 1.
Figure 3:
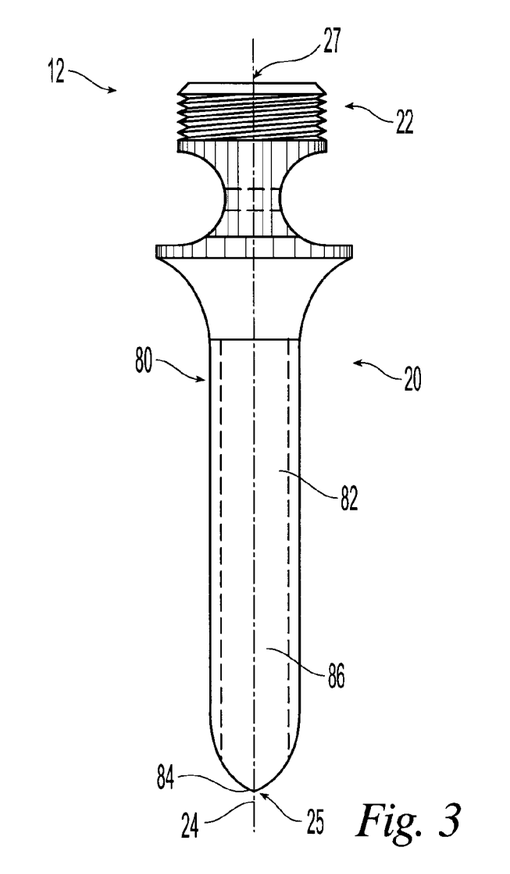
FIG. 3 is a front view of another embodiment of a fastener for the fastener assembly of FIG. 1.

Referring to FIGS. 2 and 3, lower portion 20 of fastener 12 preferably comprises a hook or pedicle screw, and has a longitudinal central axis 24 extending from a proximal end 25 to a distal end 27 and lying in a central plane. In FIG. 2, lower portion 20 comprises a hook 28 and includes a curved hook body 29 with a first end 30 connected to the upper portion 22 and a second free end 31. Hook body 29 is convex on its posterior side 32. Free end 31 runs essentially perpendicular to the central axis 24 and is adapted to the spinal geometry. As can be seen in FIG. 3, in another embodiment, lower portion 20 comprises a pedicle screw 80. Pedicle screw 80 comprises a screw body 82 with a screw point 84 and a thread 86 on the outside of the screw body 82 for engaging the vertebra. Preferably, the screw 80 is self-tapping and includes a blunt screw point 84.

Referring to FIGS. 1–4, the upper portion 22 is generally in the form of a shaft 26 extending along central axis 24 and accepts the attachment member 14 and the locking member 16. Upper portion 22 has a shoulder 33 at a first end adjacent the lower portion 20 and an external threaded portion 34 at the distal end 27 of fastener 12. At least two channels 35 traverse the shaft 26, and the channels 35 are preferably disposed on opposite sides of the central plane. The channels 35 extend orthogonal with respect to the central axis 24 and are preferably equidistant from the distal end 27. Preferably a bore 36 runs between the channels 35 transverse to the central axis 24 to facilitate the machining of a cavity 37 in the distal end 27 of fastener 12. The external threading 34 engages internal threading of locking member 16 so that locking member 16 is tightenable on the shaft 26.

Figure 4:
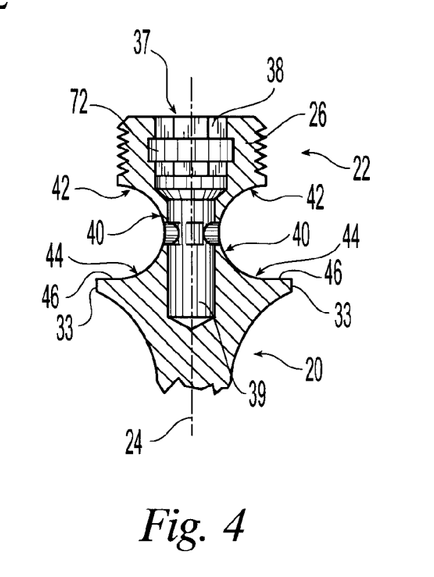
FIG. 4 is a cross-sectional view of the upper portion of a fastener of the fastener assembly of FIG. 1 taken along a central plane.

Each channel 35 is configured and dimensioned for receiving at least a portion of the longitudinal member 18. In a preferred embodiment, longitudinal member 18 is an elongate rigid rod having a circular cross-section taken in a plane extending perpendicular to the longitudinal central axis of the rod. As best seen in FIG. 4, in accordance with this embodiment, channels 35 preferably have an arcuate section 40 centrally disposed between upper 42 and lower 44 legs opening substantially laterally with respect to the central axis 24 of shaft 26. Arcuate section 40 has a diameter substantially conforming to the diameter of the rod. Preferably, the lower leg 44 extends further radially outward from the central axis 24 than upper leg 42 and defines a seat 46 for supporting a portion of the attachment member 14. Numerous other embodiments are envisioned in which the longitudinal member may have varied cross-sections, such as a rectangular bar or elliptical wire. Accordingly, channels 35 can have numerous shapes corresponding to the particular geometry of the longitudinal member used.

Referring again to FIG. 1, the attachment member 14 preferably has a generally cylindrical shape having upper 48, lower 50 and side 52 surfaces with a bore 54 extending through the upper 48 and lower 50 surfaces along central axis 24. Bore 54 extends through the attachment member 14 so that the attachment member 14 can be inserted over the external threading 34 to be positionable on the upper portion 22 of fastener 12. A slot 56 extends transversely through the attachment member 14 and is orthogonal to central axis 24 and offset from the central axis 24. Slot 56 is configured and dimensioned for receiving the longitudinal member 18 and locatable adjacent either of the channels 35 for securing the longitudinal member 18 to the upper portion 22 of fastener 12. When the longitudinal member 18 is inserted in channel 35 and attachment member 14 is assembled upon the upper portion 22, locking member 16 tightens attachment member 14 to secure the longitudinal member 18 in slot 56 and against one of the channels 35.

Locking member 16 substantially resembles a nut and has a generally disc-like shape with top 60, bottom 61 and side 62 surfaces with a hole 63 extending centrally through the top 60 and bottom 61 surfaces. The hole 63 is provided with internal threading 64 which mates with external threading 34 provided on shaft 26 of upper portion 22. As such, locking member 16 is tightenable on the shaft 26 and the bottom surface 61 contacts the upper surface 48 of the attachment member 14 to force the attachment member 14 downward toward the lower portion 20 as locking member 16 is tightened. Side surface 62 is preferably provided with a polygonal geometric configuration comprising twelve points to facilitate tightening.

Figure 5:
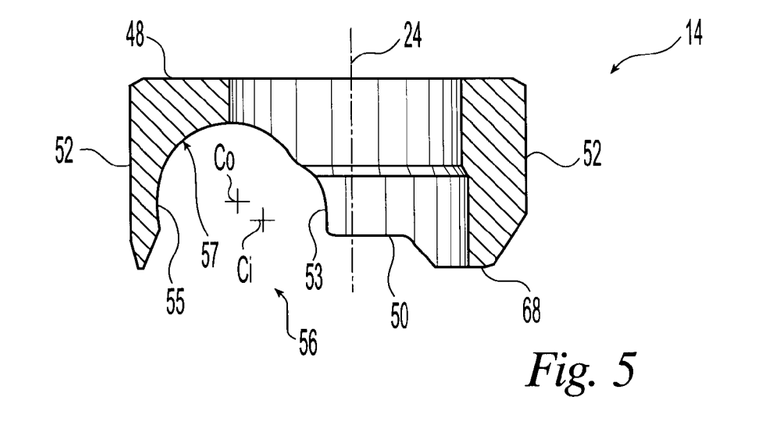
FIG. 5 is a cross-sectional view of the attachment member of the fastener assembly of FIG. 1 taken along a central plane.
Figure 6:
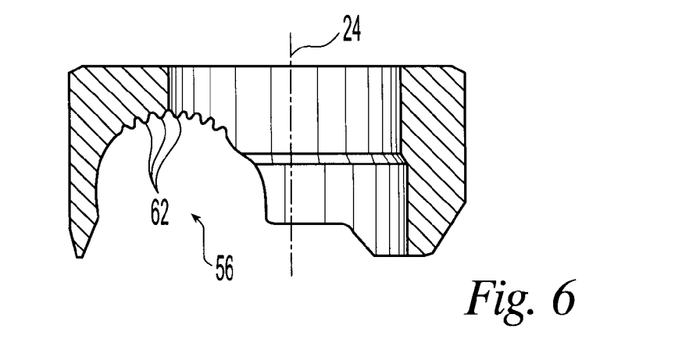
FIG. 6 is a cross-sectional view of another embodiment of the attachment member of the fastener assembly of FIG. 1 taken along a central plane.
Figure 13:
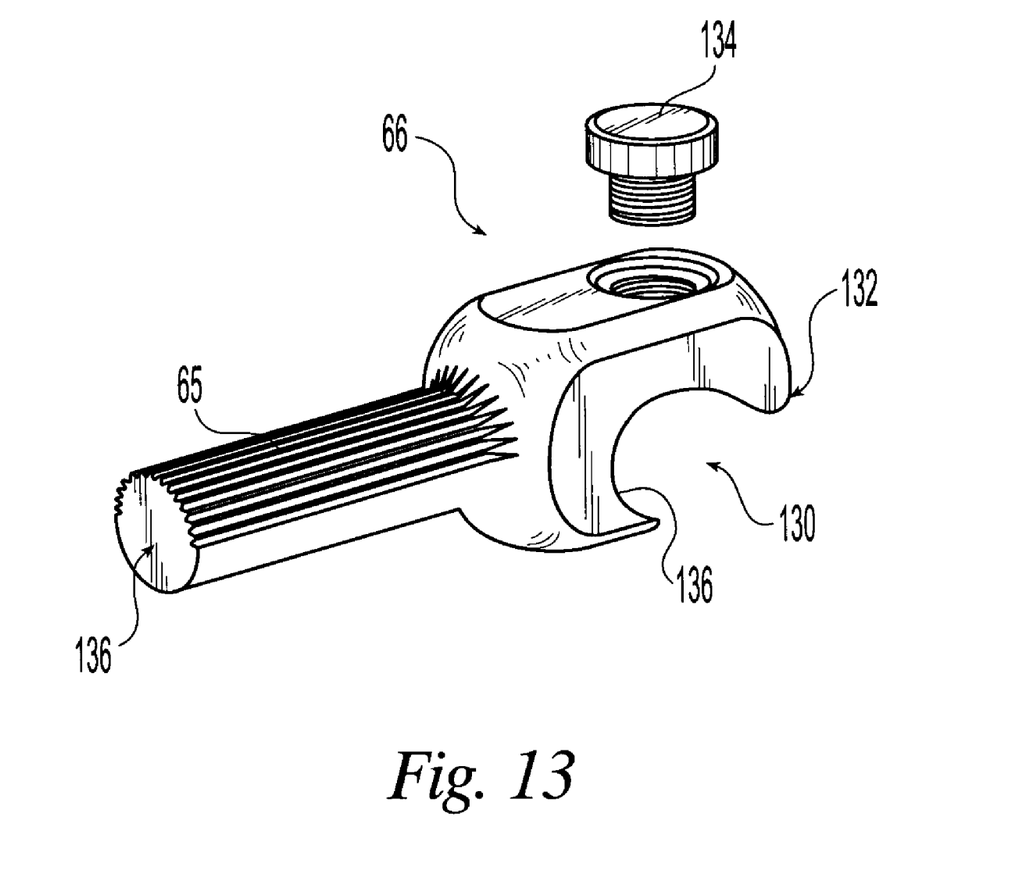
FIG. 13 is a perspective view of a transverse bar according to the present invention.

The slot 56 has a generally cylindrical cross-section and has a geometry substantially conforming to the diameter of the longitudinal member 18. Preferably, slot 56 has an eccentrically shaped cross-section. Referring to FIG. 5, slot 56 comprises multiple circular sections having centers offset with respect to one another to define an inner surface 57 towards the central axis 24 connecting inner section 53 with outer section 55. Inner and outer sections 53, 55 preferably have circular geometries. Inner section 53 has a center of curvature $C_i$ offset inward towards central axis 24 with respect to a center of curvature $C_o$ of outer section 55. The eccentric shape of inner surface 57 is useful to allow the camming of longitudinal member 18 towards the channels 35 when the attachment member 14 is tightened onto upper portion 22 as inner section 53 allows for movement of the longitudinal member axially inward to forcibly engaging the longitudinal member 18 with either of the channels 35. As can be seen in FIG. 6, in one embodiment of attachment member 14, the slot 56 includes serrations 62 along inner surface 57 for engaging corresponding ridges 65 on a ridged longitudinal member, such as transverse bar 66 (FIG. 13). In this way, the ridged longitudinal member is less likely to rotate relative to fastener 12 when the attachment member 14 is secured by locking member 16.

Figure 7:
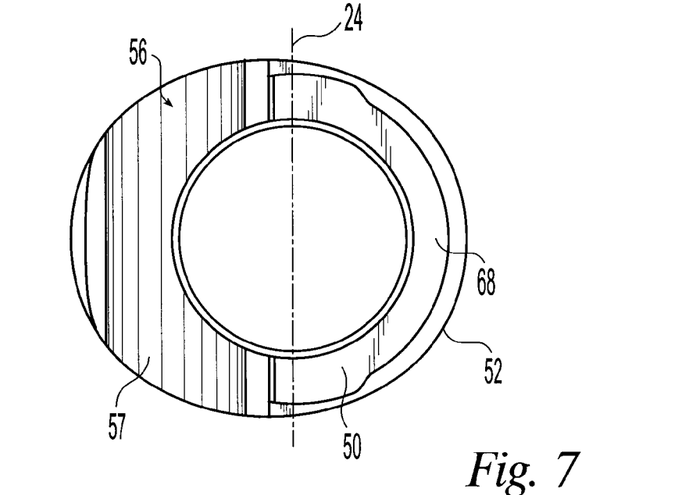
FIG. 7 is a bottom view of the attachment member of FIG. 5.

Referring to FIGS. 5–7, a protrusion 68 extends from lower surface 50 on an opposite side of the attachment member 14 from slot 56. Protrusion 68 preferably extends generally perpendicular from lower surface 50 and is spaced radially inward from the side surface 52. Also preferably, protrusion 68 runs arcuately along a portion of lower surface 50 opposite slot 56. As such, when attachment member 14 is assembled upon the upper portion 22 of fastener 12, the protrusion 68 preferably engages seat 46 for preventing the attachment member 14 from tilting when the attachment member 14 is tightened by locking member 16.

Figure 8:
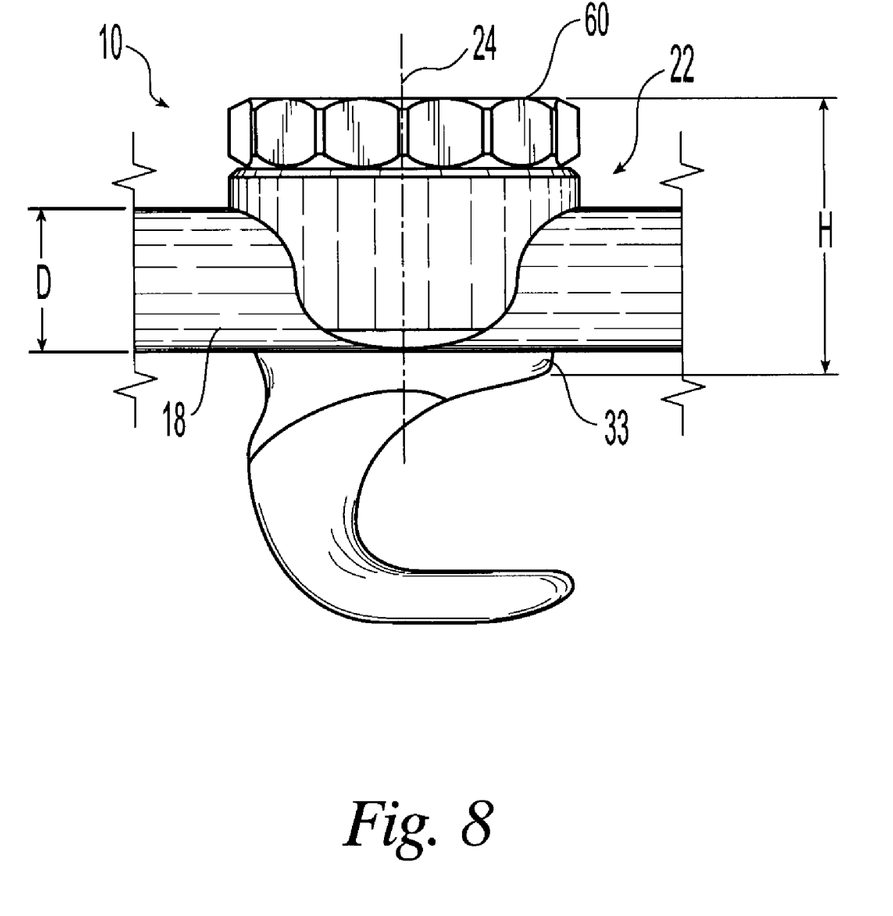
FIG. 8 is a side view of the fastener assembly of FIG. 1 showing the fastener as a hook.

As shown in FIG. 8, upper portion 22 of fastener assembly 10 has a height H measured form the base of shoulder 33 to the top surface 60 of locking member 16. Preferably height H is as minimal as possible and only slightly greater than the diameter of longitudinal member 18. Preferably height H is less than 10.0 mm. Also, preferably the ratio of longitudinal member diameter D to height H is greater than 0.50 so that the upper portion 22 has only a slightly higher profile than the longitudinal member 18. A notable advantage of maintaining such a low height H, or low profile, is that such a fastener assembly 10 is especially well suited for use in pediatric and small-statured patients.

Figure 9:
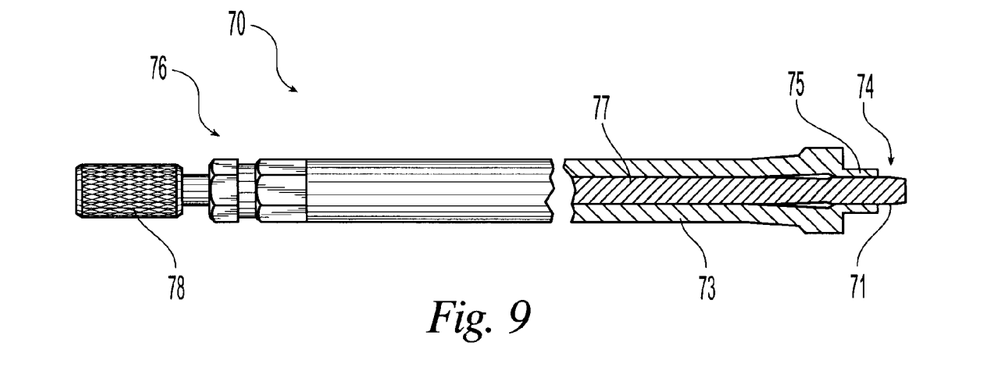
FIG. 9 is a front view of one embodiment of a manipulation device according to the present invention.

Referring again to FIG. 4, fastener 12 consists of a cavity 37 in distal end 27 opening upward and having a hexagon socket 38 near the distal end and a cylindrical hole 39 running in the direction of longitudinal central axis 24, for receiving a manipulation device 70 (FIG. 9) to facilitate the insertion of the fastener 12 into bone. Cylindrical hole 39 is preferably provided with internal threading that continues from the base of hexagon socket 38 in the direction of lower portion 20 for the positive acceptance of manipulation device 70 with corresponding external threading 71 (FIG. 9). Here, cavity 37 permits a rotationally-stable, releasable connection with manipulation device 70. Internal threading can be designed with multiple threads to strongly shorten the time required for the connection process. For this embodiment, manipulation device 70, shown in FIG. 9, consists of hollow cylindrical sheath 73 that has at its one end 74 lug 75. From the other end 76 of sheath 73, a cylindrical pin 77 can be inserted into sheath 73. Cylindrical pin 77 carries at its one end external threading 71 that, after successful insertion, protrudes beyond end 74 of sheath 73, and at its other end, grip 78 protrudes from sheath 73 and serves to tighten the connection.

Figure 10:
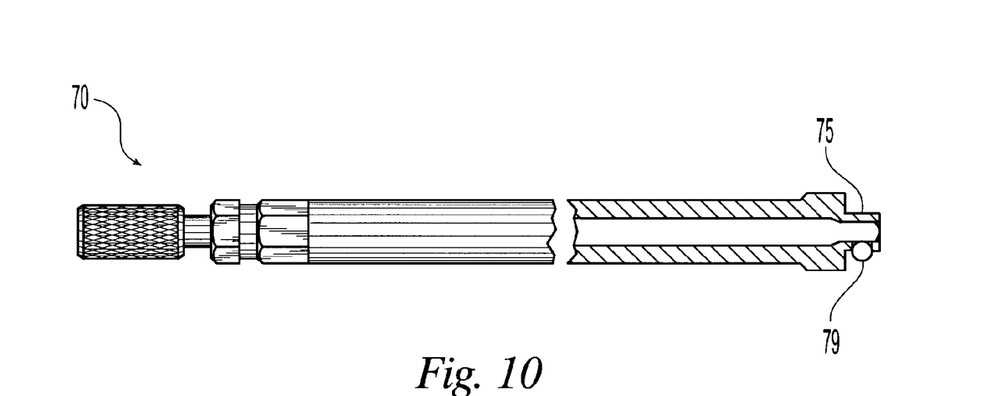
FIG. 10 is a front view of another embodiment of a manipulation device according to the present invention.

Preferably a generally rectangular groove 72 extends transverse to the hexagon socket 38 and around the circumference of the cavity 37. As shown in FIG. 10, another embodiment of the manipulation device 70 is provided with bearings 79 in lug 75 for engaging groove 72. When manipulation device 70 is introduced into cavity 37 and bearings 79 align with rectangular groove 72, pin 77 can be pushed through the sheath 73 in manipulation device 70 to press bearings 79 into rectangular groove 72. This facilitates the transfer of tensile, compressive and rotational forces via manipulation device 70 without the need to have a threaded coupling.

Figure 11:
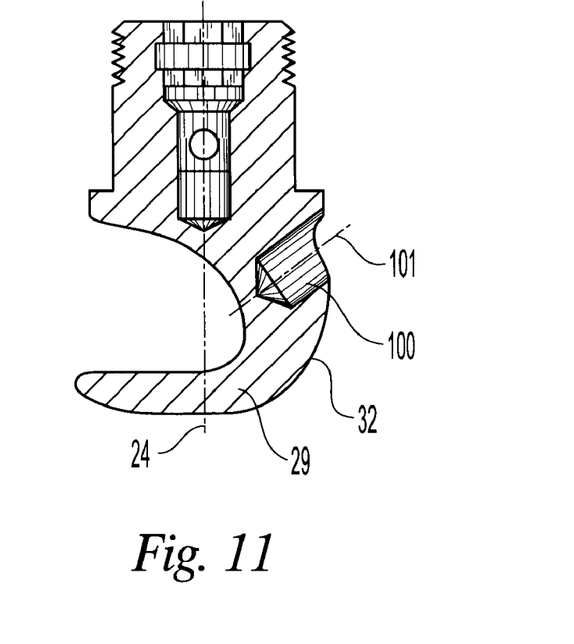
FIG. 11 is a cross-sectional view of the fastener of FIG. 2 taken along a central plane.
Figure 12:
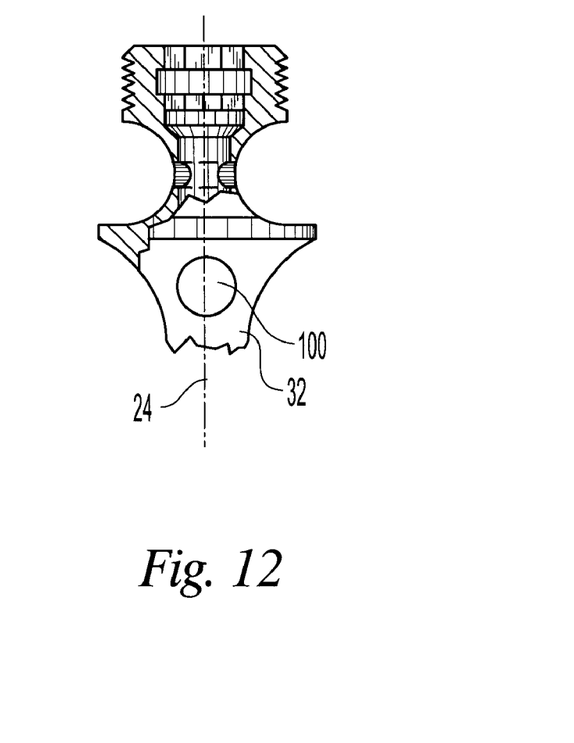
FIG. 12 is a back view of the fastener of FIG. 2.

Referring to FIG. 11, at convex posterior side 32 of hook body 29 a dimple 100 is provided to accept an installation device (not shown). Dimple 100 comprises a cylindrical hole extending along a longitudinal axis 101 at an angle with respect to the central axis 24. Referring to FIG. 12, preferably dimple 100 is located centrally with respect to the posterior side 32. In this way, dimple 100 provides an ideally suited structure for impaction to facilitate the insertion of flat end 31 into the vertebra.

Referring to FIG. 13, a transverse bar 66 is shown which may be used to secure the longitudinal member 18 to a fastener 12 that is laterally displaced from the longitudinal member 18 to avoid excessively bending the longitudinal member 18. The transverse bar 66 includes a hook 130 at one end 132. A set screw 134 extends through the hook 130 and pins the longitudinal member 18 against the inner surface 136 of the hook 134 to secure the longitudinal member 18 to the transverse bar 66. The second end 138 of the transverse bar 66 is a shaft that has ridges 65 around the circumference that mate with serrations 59 provided in attachment member 14 as described above.

In use, a plurality of fastener assemblies 10 are inserted into the vertebra along the spine with the aid of the manipulation device 70 and the longitudinal member 18 is placed in one of the two channels 35 on each of the fasteners 12. An attachment member 14 is placed onto each of the fasteners 12 so that the longitudinal member 18 is held in the channel 35 by the slot 56 of attachment member 14. A locking member 16 is then used to secure the longitudinal member 18 in the channel 35. Also, a transverse bar 66 can be secured to the longitudinal member 18 to couple the longitudinal member 18 to a laterally positioned fastener 12. In that case, the hooked end 127 of the transverse bar 66 is held to the longitudinal member 18 by a set screw 135 and the opposite end 138 of the transverse bar 66 is secured to the fastener 12 by an attachment member 14 in the same fashion as described above for the longitudinal member 18.

Because of the dual-channel structure of the fastener 12, a surgeon implementing a spinal fixation system may insert the longitudinal member 18 in either channel 35. Also, because the slot 56 is offset with respect to central axis 24, the attachment member 14 may be located on either side of fastener 12 and the longitudinal member 18 may be secured to either one of channels 35. As a result, fastener assembly 10 may be assembled on either side of the spinal column using the identical components. Further, the integral nature of the upper and lower portions 22, 20 allows for easy assembly to an already installed spinal fixation system. Because the channels 35 open laterally fastener 12 can be anchored to a vertebra and longitudinal member 18 may be laterally received in upper portion 22 and attachment member 14 can be vertically assembled thereover to secure the longitudinal member in place, and no preassembly is required.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A fastener assembly for a spinal fixation system including a longitudinal member positionable along a spinal column, the fastener assembly comprising:

a fastener including a lower portion for contacting a bone and an upper portion integral with the lower portion with a longitudinal axis extending from a proximal end to a distal end and lying in a central plane, the upper portion having two channels, wherein each channel has a lateral opening with respect to the longitudinal axis that is configured and dimensioned for receiving a portion of the longitudinal member along its perimeter;

an attachment member positionable on the fastener that at least partially covers the channel that receives the longitudinal member, and is configured and dimensioned for receiving a further portion of the longitudinal member along its perimeter; and a locking member operatively associated with the upper portion of the fastener for securing the attachment member and longitudinal member to the fastener.

2. The fastener assembly of claim 1, wherein the two channels are disposed on opposite sides of the central plane.

3. The fastener assembly of claim 2, wherein the two channels extend orthogonally with respect to the longitudinal axis and are equidistant from the proximal end of the fastener.

4. The fastener assembly of claim 3, wherein the upper portion has a bore positioned transversely to the longitudinal axis and between the two channels.

5. The fastener assembly of claim 2, wherein the attachment member comprises:

a cylinder having upper, lower and side surfaces with a bore extending through the upper and lower surfaces and defining a longitudinal axis lying in a central plane;

a slot extending through the cylinder offset from the central plane and parallel with the central plane; and a protrusion extending from the bottom surface on an opposite side of the central plane from the slot.

6. The fastener assembly of claim 5, wherein the channels define a seat for accepting the protrusion of the attachment member.

7. The fastener assembly of claim 5, wherein the slot includes serrations along the inner surface.

8. The fastener assembly of claim 5, wherein the slot has an eccentric cross-sectional shape.

9. The fastener assembly of claim 5, wherein the slot has a generally cylindrical cross-section with a geometry substantially conforming to a diameter of the longitudinal member.

10. The fastener assembly of claim 1, wherein the lower portion comprises a threaded end for engaging a vertebra.

11. The fastener assembly of claim 1, wherein the fastener includes a cavity extending longitudinally from the distal end for receiving a manipulation device.

12. The fastener assembly of claim 11, wherein the manipulation device includes a ball detent mechanism and a groove extending transversely to the cavity and around its circumference for receiving the ball detent mechanism.

13. The fastener assembly of claim 11, wherein the cavity is cylindrical and includes threads along the interior.

14. The fastener assembly of claim 1, wherein the upper portion comprises a shaft having external threads to accept the locking member.

15. The fastener assembly of claim 1, wherein the lower portion comprises a hook and includes an arcuate portion and a flat portion for facilitating implantation of the fastener.

16. The fastener assembly of claim 15, wherein the arcuate portion has a dimple on a posterior surface.

17. A spinal fixation system comprising at least one longitudinal member and the fastener assembly of claim 1.

18. A fastener assembly for a spinal fixation system including a longitudinal member positionable along a spinal column, the fastener assembly comprising:

a fastener including a lower portion for contacting a bone and an upper portion having a longitudinal axis extending from a proximal end to a distal end and lying in a central plane, the upper portion having two open channels, wherein each channel is configured and dimensioned for receiving a portion of the longitudinal member in a lateral direction with respect to the longitudinal axis;

an attachment member positionable on the fastener that at least partially covers the channel that receives the longitudinal member, and is configured and dimensioned for receiving a further portion of the longitudinal member along its perimeter and securing the longitudinal member to the fastener.

19. The fastener assembly of claim 18, wherein the two channels are disposed on opposite sides of the central plane.

20. The fastener assembly of claim 19, wherein the two channels extend orthogonally with respect to the longitudinal axis and are equidistant from the proximal end of the fastener.

21. The fastener assembly of claim 18, wherein the lower portion comprises a hook.

22. The fastener assembly of claim 18, wherein the lower portion comprises a threaded end for engaging a vertebra.

23. A spinal fixation system comprising at least one longitudinal member and the fastener assembly of claim 18.

24. A fastener assembly for a spinal fixation system including a longitudinal member positionable along a spinal column, the fastener assembly comprising:

a fastener including a lower portion for contacting a bone and an upper portion with a longitudinal axis extending therethrough, the upper portion having two substantially semicircular grooves, wherein each groove is configured and dimensioned for receiving a portion of the longitudinal member in a lateral direction with respect to the longitudinal axis;

an attachment member positionable on the fastener that at least partially covers the channel that receives the longitudinal member, and is configured and dimensioned for receiving a further portion of the longitudinal member along its circumference and securing the longitudinal member to the fastener.

25. A kit for a spinal fixation system, comprising:

a longitudinal member positionable along a spinal column; and a fastener assembly, comprising:

a fastener including a lower portion for contacting a bone and an upper portion integral with the lower portion with a longitudinal axis extending from a proximal end to a distal end and lying in a central plane, the upper portion having two channels, wherein each channel has a lateral opening with respect to the longitudinal axis that is configured and dimensioned for receiving a portion of the longitudinal member along its perimeter;

an attachment member positionable on the fastener that at least partially covers the channel that receives the longitudinal member, and is configured and dimensioned for receiving a further portion of the longitudinal member along its perimeter; and a locking member operatively associated with the upper portion of the fastener for securing the attachment member and longitudinal member to the fastener.

26. The kit of claim 25, comprising at least two longitudinal members.

27. The kit of claim 25, comprising at least two fastener assemblies.

28. The kit of claim 25, comprising at least two longitudinal members and at least two fastener assemblies.

* * * * *